United States Patent [19]

Zinreich et al.

[11] Patent Number: 5,469,847
[45] Date of Patent: Nov. 28, 1995

[54] RADIOGRAPHIC MULTI-MODALITY SKIN MARKERS

[75] Inventors: Simion J. Zinreich; Eva S. Zinreich, both of Owings Mill, Md.; Rex O. Bare, Lake Forest, Calif.

[73] Assignee: IZI Corporation, Owings Mills, Md.

[21] Appl. No.: 204,882

[22] Filed: Feb. 28, 1994

Related U.S. Application Data

[63] Continuation of Ser. No. 942,508, Sep. 9, 1992, abandoned.

[51] Int. Cl.[6] ............................ A61B 5/055; A61B 6/03
[52] U.S. Cl. ........................... 128/653.1; 128/653.2; 128/653.5; 156/145; 156/242; 264/250; 378/162; 378/163; 324/309
[58] Field of Search ........................ 128/653.1, 653.2, 128/653.5, 639, 640, 641; 156/145, 146, 242; 324/308, 309; 356/347, 348; 264/250, 259; 378/162, 163, 164, 165; 250/370.1

[56] References Cited

U.S. PATENT DOCUMENTS

| | | |
|---|---|---|
| 1,168,177 | 1/1916 | de Yoanna . |
| 2,462,018 | 2/1949 | Wood . |
| 3,977,392 | 8/1976 | Manley ................................ 128/641 |
| 3,998,215 | 12/1976 | Anderson et al. .................. 128/641 |
| 4,506,676 | 3/1985 | Duska . |
| 4,583,538 | 4/1986 | Onik et al. . |
| 4,617,935 | 10/1986 | Cartmell et al. .................... 128/641 |
| 4,710,875 | 12/1987 | Nakajima et al. .................. 378/162 |
| 4,774,957 | 10/1988 | Nambu et al. ................... 128/653.2 |
| 4,813,062 | 3/1989 | Gilpatrick . |
| 4,827,931 | 5/1989 | Longmore . |
| 4,827,939 | 5/1989 | Cartmell et al. .................... 128/640 |
| 4,860,331 | 8/1989 | Williams . |
| 4,985,019 | 1/1991 | Michaelson . |
| 5,071,602 | 12/1991 | Nambu et al. ................... 128/653.5 |
| 5,193,106 | 3/1993 | DeSena ................................ 378/163 |
| 5,205,297 | 4/1993 | Montecalvo et al. ............... 128/641 |
| 5,209,233 | 5/1993 | Holland et al. ..................... 128/671 |

FOREIGN PATENT DOCUMENTS

1088706  4/1985  U.S.S.R. ......................... 128/653.1

*Primary Examiner*—Krista M. Zele
*Attorney, Agent, or Firm*—Lyon & Lyon

[57] ABSTRACT

The device of the present application is an adhesive surface marker comprising a gel sealed by a casing and membrane structure. The markers of the present invention can include a cavity for receiving imaging materials. The markers provide means for marking patients and diagnostic images taken of those patients through different methods including X-Ray, Computerized Tomography, Positron Emission Tomograph, and Nuclear Magnetic Resonance Imaging among others, retain their shape and size, and do not suffer from water-loss which can lead to reduced density to certain radio-graphic modalities (e.g. MRI).

6 Claims, 2 Drawing Sheets

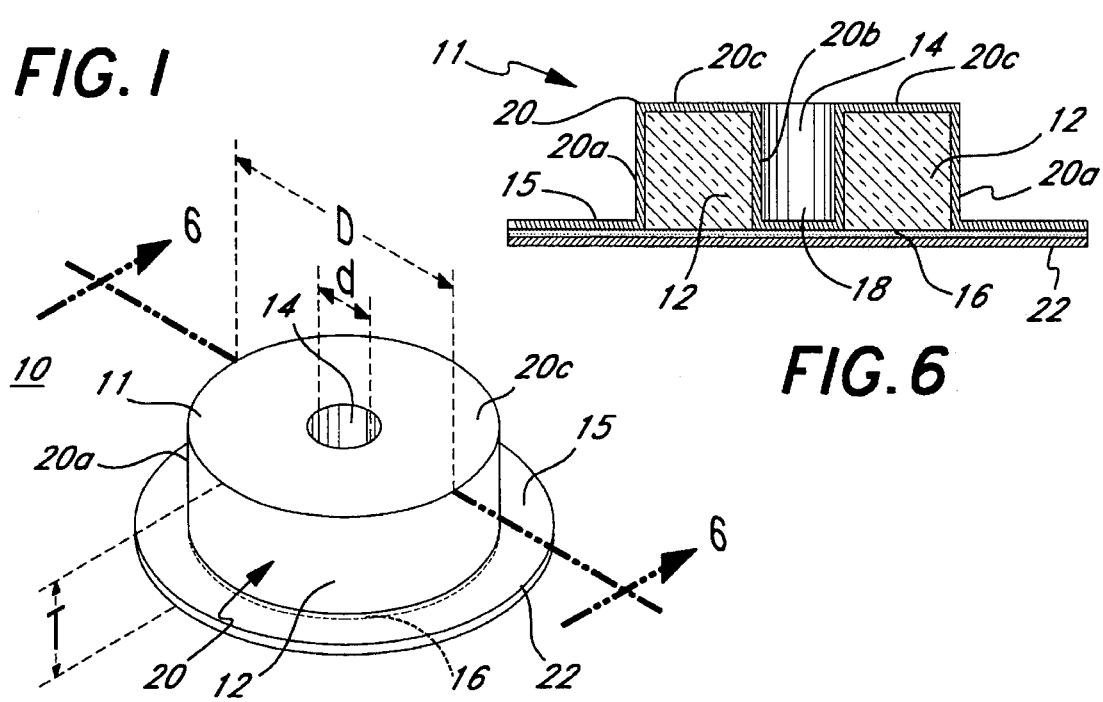
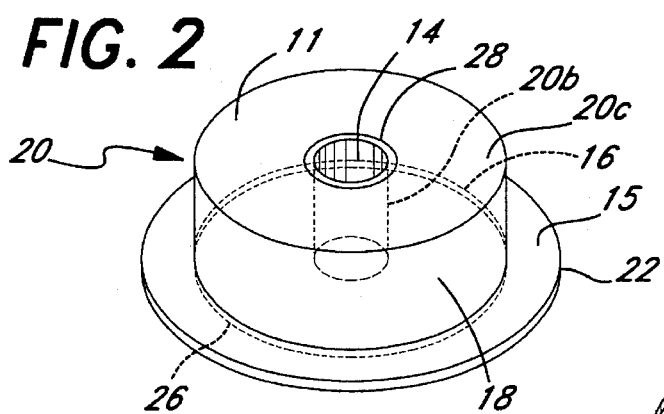
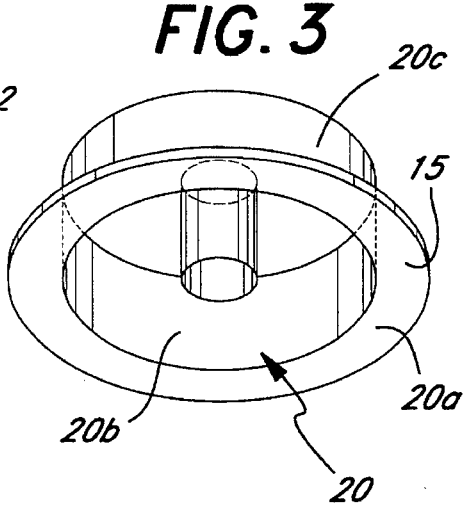
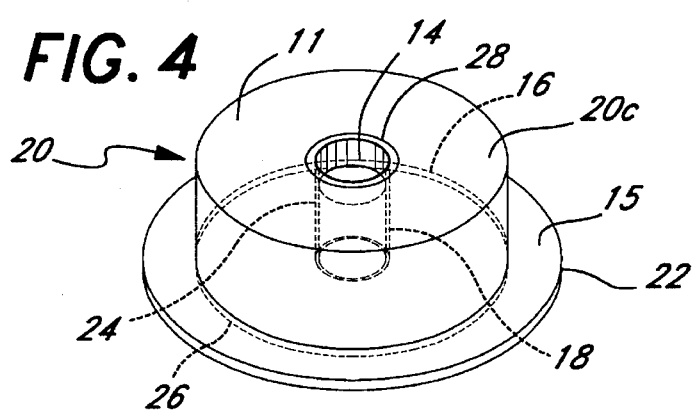

RADIOGRAPHIC MULTI-MODALITY SKIN MARKERS

RELATED APPLICATION

This is a continuation of application Ser. No. 07/942,508, filed on Sep. 9, 1992, now abandoned and which designated the U.S.

This application is related to application Ser. No. 06/942,715, filed Sep. 9, 1992 (concurrently herewith), now U.S. Pat. No. 5,368,030, entitled Non-Invasive Multi-Modality Radiographic Surface Markers" by S. James Zinreich, Eva S. Zinreich, and David C. Howson.

FIELD OF THE INVENTION

The present application relates to radiographic surface markers, particularly improved non-invasive radiographic surface markers useful in multiple diagnostic techniques.

BACKGROUND

Radiologists and others use a number of methods to create images of structures within a patient's body to help diagnose diseases and guide therapeutic procedures. Methods used include, for example, conventional X-Ray, Computerized Tomography ("CT"), ultrasound, Positron Emission Tomography ("PET"), and (Nuclear) Magnetic Resonance Imaging ("NMR" or "MRI"), among others. These methods respectively employ X-radiation (both the X-Ray and CT methods), sound, radio active emissions, and magnetic fields in combination with radio-frequency electromagnetic radiation, to create images of structures within the patient's body.

When creating such diagnostic images of a patient, it is desirable to use surface anatomical features which are visible both on the patient and on the diagnostic image of that patient as reference points to facilitate the performance of surgical or other therapeutic intervention techniques. Reference points defined on both a patient's body and a diagnostic image of interior features of that patient's body, allow a physician to geometrically calculate the precise location of a particular site within the patient's body or a particular position of a specific structure within the patient's body. Pin-pointing the location of a particular site or structure allows the physician to more easily and accurately biopsy or otherwise treat the area.

However, there often are no surface anatomical features on the patient's body adequate to use as such reference points (e.g. such features may not exist or may not be located appropriately for such use). If there are no anatomical reference points on the surface of the patient's body, one is unable to precisely locate a target site or structure shown in a two dimensional diagnostic image. The location of the target site or structure is obscure because the two-dimensional diagnostic image does not provide sufficient information for a geometric relationship between a surface point on the patient's body and the target site or structure to be accurately calculated (i.e. it is unclear at what point on the patient's body the diagnostic image scan was taken).

In such cases, it is desirable to place artificial reference markers on the patient's skin to serve as reference points. A physician may place artificial markers in positions which are optimal reference points relative to the location of target tissues within the patient's body. The markers are designed to clearly show unique and identifiable reference points on both the surface of the patient's body and on the diagnostic image.

In addition, it is becoming increasingly important to align images formed by different imaging methods to better identify pathologic structures. Aligning, or "rectifying," images and other radiographic data formed by different imaging methods would be substantially improved (in both ease and accuracy) through the use of surface markers which create reference points visible to a multiplicity of imaging methods. Such surface markers would facilitate the precise superimposition of imaging data from CT, MRI, and other sources for optimal correlation of tissues and physiologic processes which are demonstrated using these various methods.

Furthermore, it is desirable to provide reference markers of consistent shapes and sizes to facilitate the above described calculations and methods.

Imaging with X-radiation (X-rays and CT scans) requires that a reference marker comprise a material which impedes the transmission of radiation at the wavelength used in commercial machines. Metals and materials which contain metal salts are popular for these techniques. However, certain organic materials, and other non-metallic materials also have adequate opacity.

A reference marker for use with MRI depends on entirely different properties. With this modality, a powerful magnetic field is applied which orients the rotational axis of atomic nuclei along a single vector. Upon removal of the magnetic field, the spinning nuclei revert to a random distribution of axial orientation. In the process of reverting the nuclei emit radiation at characteristic frequencies. By detecting this radiation a computer, using mathematical formulae, can compose an image based on the different intensities from different tissues.

Reference markers for use with MRI require mobile atomic nuclei in a liquid state. Commercial MRI machines also detect frequencies and intensities of radiation typically emitted from aqueous solutions or composites. Certain organic compounds also emit frequencies detectable by commercial machines. Therefore, it is important that markers retain atomic nuclei in an aqueous state (e.g. it is important that markers do not lose water) to be dense to MRI.

Surface markers of various shapes and sizes are generally shown in the prior art. However, such prior art surface markers are inadequate to address the problems described above. There is no surface marker disclosed which is satisfactorily visible to a variety of imaging methods. For example, one commercial product today uses a small, dense metal bead attached to adhesive tape. The metal is dense to X-radiation and the adhesive allows rapid, secure attachment to the patient's skin. However, the metal produces an imaging artifact at certain useful X-radiation intensities and it is transparent to methods such as MRI. Moreover, with MRI an aberration is produced which obscures adjacent tissue, rendering the image useless. Therefore, this surface marker is not satisfactory.

It would be useful to have a marker which is dense to all of the commonly used imaging methods, which does not produce aberrations that obscure portions of the image, and which is available in consistent and reliable shapes and sizes.

SUMMARY OF THE INVENTION

A preferred embodiment of the present application comprises improved radiographic multiple modality surface markers which are appropriate to use as artificial reference points and which are visible both on a patient and on diagnostic images taken by various methods. The improved multi-modality surface markers of the present invention comprise a gel, preferably a hydro-gel, sealed on all sides to prevent water loss and thereby provide markers with consistent and reliable sizes and shapes, to eliminate contact of the gel with other surfaces, and to provide for easy sterilization of the markers. The improved multi-modality surface markers of the present invention are visible to many imaging methods and do not produce undesirable images which obscure portions of desirable images.

Accordingly, it is a principal object of the present invention to provide improved surface markers for use as reference points on diagnostic images and which comprise a gel which is dense to multiple imaging methods such as X-Ray, CT, ultrasound, PET, MRI, and others, which does not produce undesirable aberrations which obscure portions of the diagnostic images, and which is sealed.

It is a further object of the present invention to provide improved multi-modality surface markers comprising a gel which is sealed on all sides thereby preventing water-loss from the gel and providing markers of consistent sizes and shapes.

It is an additional object of the present invention to provide improved multi-modality surface markers comprising a gel which is sealed on all sides such that contact of the gel with other surfaces is eliminated.

It is another object of the present invention to provide improved multi-modality surface markers comprising a gel which is sealed on all sides such that a chamber may be provided which allows for the injection of additional materials into the chamber without the materials directly contacting the gel.

It is still a further object of the present invention to provide improved multi-modality surface markers comprising a gel which is sealed on all sides such that sterilization of the markers is easily accomplished.

BRIEF DESCRIPTION OF THE DRAWINGS

FIG. 1 shows a perspective view of a multi-modality surface marker of the present application.

FIG. 2 shows a perspective view of the surface marker of FIG. 1 with the core shown in phantom and a disk attached to the bottom of the marker.

FIG. 3 is a perspective view showing the bottom of an outer casing of the marker of the present invention.

FIG. 4 shows a perspective view of the surface marker of FIG. 2 with a porous matrix trapped inside the central well.

FIG. 6 shows a cross-sectional view of the surface marker of FIG. 1.

DETAILED DESCRIPTION OF THE PREFERRED EMBODIMENT

Figure 5:
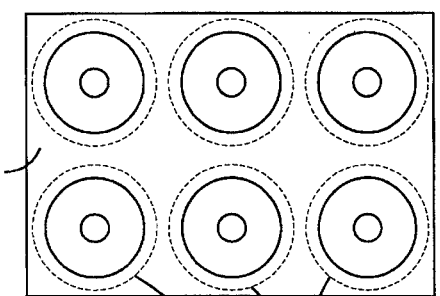
FIG. 5 shows a plan view of a set of six surface markers of the present invention.

A multi-modality surface marker 10 of the present invention comprises an improved disk-like marker 10 (FIG. 1) comprising a gel 12 (FIGS. 1 and 6) which is sealed on all sides by an outer casing 20 (FIG. 3), preferably comprising a flexible material, and a membrane 16 (FIGS. 1 and 6). The gel 12 has a mobile phase suitable for MRI imaging by commercial machines and is sufficiently X-Ray-opaque for adequate imaging on CT or X-Ray. As shown in FIGS. 3 and 6, the outer casing 20, which may be vacuum or pressure formed, comprises an outer cylindrical wall 20a and an inner cylindrical wall 20b with an integrally formed top wall 20c.

Figure 7:
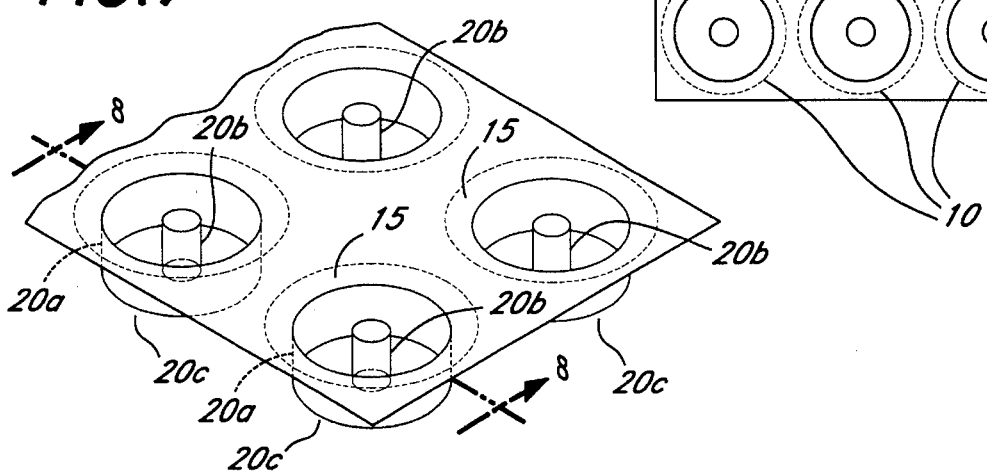
FIG. 7 shows a perspective view of a sheet of outer casings of the present invention.
Figure 8:
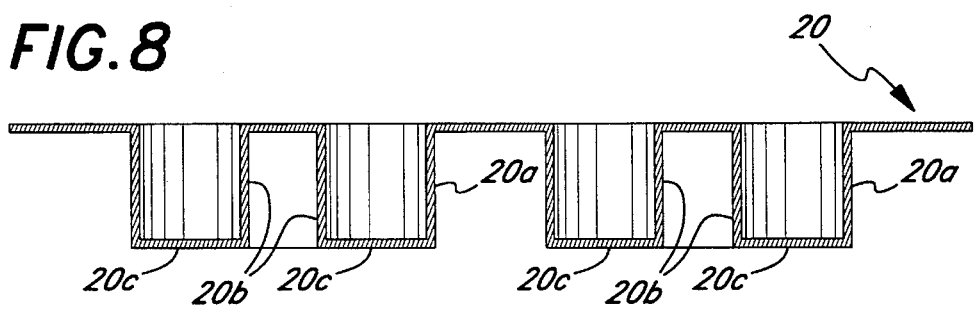
FIG. 8 shows a cross-sectional view of the sheet of outer casings of FIG. 7.
Figure 9:
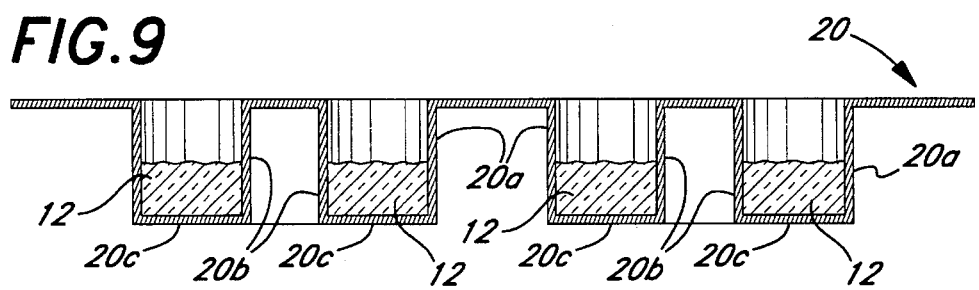
FIG. 9 shows a cross-sectional view of the sheet of outer casings of FIG. 7 as gel is being introduced into the casing cavities.
Figure 10:
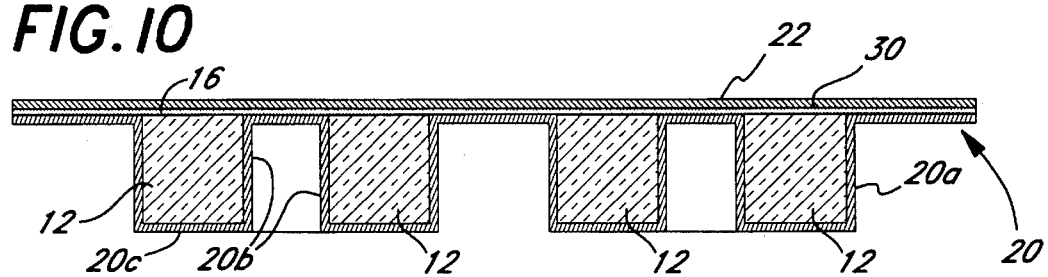
FIG. 10 shows a cross-sectional view of the sheet of outer casings of FIG. 7 with gel filled therein, a membrane layer, an adhesive layer, and an outer backing attached thereto.

As shown in FIGS. 7–10, the surface marker 10 of the present invention is formed up-side-down. During manufacture of the marker 10 the top wall 20c is positioned on the bottom so that the outer casing 20 forms a moat into which the gel 12 may be poured (FIGS. 7 and 8). Multiple outer casings 20 may be formed from a single sheet material (FIG. 7). Thus, multiple markers 10 can be formed simultaneously. The marker 10 is preferably formed by injecting, pouring, or laying the gel 12 (while in a fluid state) into the formed outer casing 20 (FIG. 9), laminating a thin membrane layer 16 over the gel 12 to seal it in the casing 20 (FIG. 10), allowing the gel 12 to set, applying adhesive 30 and a removable backing 22 to the membrane layer 16 by methods well known in the art (FIG. 10), and die cutting the markers 10 so they may be individually removed and used. In addition, as shown in FIGS. 5 and 10, multiple markers 10 can be attached to a single backing 22. The markers 10 are die cut so as to provide a lip 15 of casing material (FIGS. 1–4, 6, and 7). The lip 15 provides sufficient contact surface area to adequately hold the markers 10 to a surface.

As shown in FIG. 6, the gel 12 of the improved marker 10 of the present invention is sealed on all sides (by the outer casing 20 (i.e. 20a, 20b, and 20c) on the sides and the top and by the thin membrane 16 on the bottom) which prevents water evaporation from the gel 12 and eliminates contact of the gel 12 with other surfaces. Reduction of water loss is important because water loss could affect the marker's density to certain radiographic modalities (e.g. MRI) and could affect the marker's size or shape.

A material suitable for gel 12 is a proprietary hydrogel manufactured by Omnica Corporation of Irvine, Calif. However, other commercially-produced materials can be used and other materials could be developed which would also work well.

As shown in FIG. 1, the marker 10 of the present invention comprises a circular disk 12 approximately fifteen millimeters in outer diameter D and approximately three millimeters thick T made from a gel 12 within an outer casing 20. As shown in FIG. 6, the outer casing 20 encloses the sides and the top of the marker 10 while the membrane 16 encloses the bottom. As shown in FIGS. 1 and 6, the marker 10 has a center comprising a central axial hole 14 of approximately four millimeters in diameter d which forms a mouth for a central well 18. The central well 18 is defined by the inner cylindrical walls 20b of the outer casing 20. Thus, although the marker 10 is perforated, the gel 12 is completely surrounded.

As shown in FIG. 2, when the marker 10 is to be used with PET scans the central well 18 is enclosed by membrane 16 and an optional plastic disk 26 on the bottom, an additional membrane 28 on the top, and the inner cylindrical walls 20b of the outer casing 20 on the sides to seal the central well 18 so it is capable of containing liquid. A liquid imaging agent can be injected into the sealed well 18, using a conventional hypodermic needle, through the top membrane 28 thereby making the marker 10 visible to PET scans. The inner cylindrical wall 20b of the marker 10 prevents the liquid in the well 18 from contacting the gel 12. The plastic disk 26 prevents the hypodermic needle from extending through the bottom of the marker 10.

A user typically will obtain a package which contains multiple markers 10 on a stiff film backing 22 (FIG. 5). To use the markers 10, the user will open a package containing the markers 10 and take out the film backing 22 which carries the markers 10. The user will then remove a marker 10 from the backing 22 and apply it to the desired location on a patient's skin. One or more markers 10 may be so applied depending on the procedures to be used and the reference points desired.

In images created from either MRI or X-Ray modalities (including CT) a marker 10 appears in side view as a heavy, bright line on a negative image or a heavy, dark line on a positive image. If the image is taken perpendicular to a top surface 11 of the marker 10, the marker 10 appears as a bright disk shape on negative images or as a dark disk shape on positive images.

With scanned images, such as CT or MRI, the plane of the scan would typically pass through a marker 10 perpendicular to the plane of the surface 11 of the marker 10 thereby slicing through the marker 10. Therefore, scanned images generally show the marker 10 in cross-section normal to the marker surface 11.

A first scan that intersects the marker 10 shows on an image as a very short line or dot because the scan intersected the marker 10 through a short section. A second scan shows on an image as a longer line because a longer section of the marker 10 is intersected by the scan. As the scans begin to intersect the marker 10 near the marker's center 13, the image of the marker 10 shows a gap due to the scan intersecting the central hole 14. A scan through the center of the marker 10 shows the widest gap in the image due to the scan intersecting the marker 10 through the center of the central hole 14 where the hole 14 is the widest. One may measure the size of the gap present in an image and thereby directly visualize the spatial relationship between the central hole 14 of the marker 10 and any underlying structures or pathology of the patient.

By using multiple markers and multiple scans one may precisely triangulate the location of deep structures of the patient relative to the array of surface markers 10. These relationships may then be used to guide a surgical approach or other medical procedures. For example, the central holes 14 of the markers 10 (without the plastic disks 26) are designed to permit passage of needles or other instruments for sampling tissues or for surgically ablating tissues the positions of which are calculated relative to the central hole 14. Optionally, a perforation (not shown) may extend through the membrane 16 in the area of the hole 14 to facilitate needle passage.

Utilizing the markers 10 as described above, requires accurate and consistent measurements of the images in the radiograph and of the markers 10 on the patient. If the markers 10 are not of consistent size and shape, it may be difficult to accurately determine the location of the marker 10 and, therefore, the location of a deep structure which is calculated from the location of the marker 10. For example, if a marker 10 was irregularly or unevenly shaped, it may be difficult to determine the outer limits of the marker 10 and, therefore, difficult to make accurate measurements and calculations. Inaccuracies may also occur if a marker 10 changed shape or size between the time a radiograph was taken and the time a procedure was performed.

The present marker 10 precludes these problems by providing a marker 10 comprising a gel 12 which is completely sealed and, therefore, protected from water-loss which could lead to reduced density and change of shape or size. The outer casing 20 of the present invention provides the added benefit of establishing boundary walls for the marker 10 and, therefore, the markers 10 are evenly and regularly shaped and sized.

The markers 10 may optionally be sterilized or provided by the manufacturer sterile. Sterilization of the markers 10 avoids potential infection of a patient due to an accidental passage of infectious organisms from the surface of the marker 10 and avoids contamination of the sterile field prepared on a patient prior to a biopsy procedure. The markers 10 of the present invention are easily sterilized because the gel 12 is completely sealed and, therefore, will not leak out or stick to surfaces during the sterilization procedures.

The nature of the preferred material (the gel 12) readily permits the production of a wide variety of two- and three-dimensional shapes for use in particular procedures. The marker 10 shown and described above represents some commonly useful embodiments. Other embodiments use composites of different materials to achieve the objectives of providing multi-modal imaging, self-adhesion, and useful geometric shapes. For example, an X-Ray-opaque metal, metallic powder or particles, or metallic salt (e.g. barium sulfate) may be laid into the outer casing 20 in addition to the gel 12. Other materials may include materials and shapes which may be visible through MRI or other modalities.

Liquid materials may also be used to provide optimal visible density on MRI or other imaging modalities. Such liquids can be captured within the outer casing 20, within the central well 18, or on a porous matrix of a moisture-retentive material 24, such as a sponge, included in the central well 18 of a marker 10. As shown in FIG. 4, in one such embodiment, the central well 18 of the marker 10 contains a sponge-like matrix 24. The chamber 18 is closed by a membrane 28 on the top, a membrane 16 and an optional rigid disk 26 on the bottom, and the inner cylindrical wall 20*b* of the outer casing 20 on the sides. In one use of this marker 10, a user prepares a nuclide such as those known and used in PET scans. The user then injects a small volume of the nuclide into the sponge-like matrix 24 contained in the closed chamber 18 by penetrating the top membrane 28 with a hypodermic needle. The top membrane 28 retains the liquid within the sponge-like matrix 24, the bottom membrane 16 and plastic disk 26 also retain the liquid and prevent the needle from protruding through the marker 10 into the patient's skin, and wall 20*b* of the outer casing 20 prevents the nuclide from contacting the gel 12. The patient is then ready to be scanned.

While embodiments of the present invention have been shown and described, various modifications may be made without departing from the scope of the present invention, and all such modifications and equivalents are intended to be covered.

What is claimed is:

1. A radiographic surface marker comprising a casing comprising inner side walls, outer side walls, and top walls, said inner, outer, and top walls defining a first chamber and a second chamber, said first chamber holding dense material visible to multiple radiographic imaging methods, a first membrane attached to said casing forming a bottom wall and sealing the dense material into said first chamber, a second membrane attached to said casing sealing said second chamber and enabling later injection of material into said second chamber without said later injected material contacting said dense material, and a disk attached to at least one of said first membrane and said second membrane for providing a needle stopping surface.

2. The radiographic surface marker of claim 1 further comprising an adhesive layer for adhering the marker to a patient.

3. A radiographic surface marker comprising a casing comprising inner side walls, outer side walls, and top walls, said inner, outer, and top walls defining a first chamber and a second chamber, said first chamber holding dense material visible to multiple radiographic imaging methods, a first membrane attached to said casing forming a bottom wall and sealing the dense material into said first chamber, a second membrane attached to said casing sealing said second chamber and enabling later injection of material into said second chamber without said later injected material contacting said dense material, and a porous material contained in said second chamber.

4. The radiographic surface marker of claim 3 wherein a material opaque to Positron Emission Tomography is injected into the porous material in the second chamber.

5. The radiographic surface marker of claim 3 further comprising a disk attached to at least one of said first membrane and said second membrane for providing a needle stopping surface.

6. The radiographic surface marker of claim 3 further comprising an adhesive layer for adhering the marker to a patient.

* * * * *

UNITED STATES PATENT AND TRADEMARK OFFICE
CERTIFICATE OF CORRECTION

PATENT NO. : 5,469,847
DATED : November 28, 1995
INVENTOR(S) : ZINREICH, S. James et al.

It is certified that error appears in the above-indentified patent and that said Letters Patent is hereby corrected as shown below:

```
Column 1, line 9, please delete "06/942," and
insert --07/942,-- therefor.
```

Signed and Sealed this

Nineteenth Day of March, 1996

Attest:

BRUCE LEHMAN

Attesting Officer     Commissioner of Patents and Trademarks